United States Patent
Stedman (10) Patent No.: US 7,930,931 B2
(45) Date of Patent: Apr. 26, 2011

(54) SYSTEM AND METHOD FOR QUANTIFYING THE PRESENCE OF COMPONENTS IN THE EXHAUST OF COMMERCIAL AND/OR HEAVY-DUTY VEHICLES

(75) Inventor: Donald H. Stedman, Denver, CO (US)

(73) Assignee: Environmental Systems Products Holdings Inc., East Granby, CT (US)

( * ) Notice: Subject to any disclaimer, the term of this patent is extended or adjusted under 35 U.S.C. 154(b) by 259 days.

(21) Appl. No.: 12/114,189

(22) Filed: May 2, 2008

(65) Prior Publication Data

US 2009/0272181 A1 Nov. 5, 2009

(51) Int. Cl.
*G01M 15/10* (2006.01)
(52) U.S. Cl. .................................................. 73/114.71
(58) Field of Classification Search ................ 73/114.71
See application file for complete search history.

(56) References Cited

U.S. PATENT DOCUMENTS

| | | | |
|---|---|---|---|
| 2,658,434 A | 11/1953 | Miller | |
| 2,726,594 A | 12/1955 | Cooper et al. | |
| 3,439,527 A | 4/1969 | Rohrer | |
| 4,216,710 A * | 8/1980 | Asmus | 454/49 |
| 4,704,897 A | 11/1987 | Kawase et al. | |
| 4,924,095 A * | 5/1990 | Swanson, Jr. | 250/338.5 |
| 4,979,390 A | 12/1990 | Schupack et al. | |
| 5,046,353 A | 9/1991 | Thompson | |
| 5,167,146 A | 12/1992 | Hostetter | |
| 5,210,702 A * | 5/1993 | Bishop et al. | 702/24 |
| 5,252,828 A | 10/1993 | Kert et al. | |
| 5,291,265 A | 3/1994 | Kebabian | |
| 5,319,199 A * | 6/1994 | Stedman et al. | 250/338.5 |
| 5,343,043 A | 8/1994 | Johnson | |
| 5,369,976 A | 12/1994 | Ratton | |
| 5,371,367 A | 12/1994 | DiDomenico et al. | |
| 5,388,453 A | 2/1995 | Ratton et al. | |
| 5,401,967 A | 3/1995 | Stedman et al. | |
| 5,414,626 A | 5/1995 | Boorse et al. | |
| 5,418,366 A | 5/1995 | Rubin et al. | |
| 5,469,731 A * | 11/1995 | Decker et al. | 73/23.31 |
| 5,488,875 A | 2/1996 | Adair | |
| 5,489,777 A | 2/1996 | Stedman et al. | |
| 5,498,872 A | 3/1996 | Stedman et al. | |
| 5,583,765 A | 12/1996 | Kleehammer | |

(Continued)

FOREIGN PATENT DOCUMENTS

EP 0 681 179 A1 11/1995
(Continued)

OTHER PUBLICATIONS

Zahniser, Mark S., et al., "Measurement of Trace Gas Fluxes Using Tunable Diode Laser Spectroscopy", *Phil. Trans. R. Soc. Lond. A*, vol. 351, 1995, pp. 371-382.

(Continued)

*Primary Examiner* — Freddie Kirkland, III
(74) *Attorney, Agent, or Firm* — Pillsbury Winthrop Shaw Pittman LLP (57) ABSTRACT

A system and/or method for quantifying the presence of one or more components in vehicle exhaust, and more particularly to a non-contact, extractive sampling system and method for quantifying the presence of one or more components in exhaust emissions of commercial and/or heavy-duty vehicles that emit exhaust at an elevated level, under actual operating conditions.

21 Claims, 3 Drawing Sheets

U.S. PATENT DOCUMENTS

| | | | | |
|---|---|---|---|---|
| 5,589,629 | A | * | 12/1996 | Quinn .......................... 73/23.31 |
| 5,591,975 | A | * | 1/1997 | Jack et al. .................. 250/338.5 |
| 5,644,133 | A | | 7/1997 | Didomenico et al. |
| 5,693,872 | A | * | 12/1997 | Quinn .......................... 73/23.31 |
| 5,719,396 | A | | 2/1998 | Jack et al. |
| 5,726,450 | A | * | 3/1998 | Peterson et al. ........... 250/338.5 |
| 5,797,682 | A | * | 8/1998 | Kert et al. ..................... 374/123 |
| 5,831,267 | A | * | 11/1998 | Jack et al. .................. 250/338.5 |
| 5,877,862 | A | | 3/1999 | Nelson et al. |
| 6,025,920 | A | | 2/2000 | Dec |
| 6,306,031 | B1 | * | 10/2001 | Hansen et al. .................. 454/64 |
| 6,307,201 | B1 | | 10/2001 | Didomenico et al. |
| 6,455,851 | B1 | * | 9/2002 | Lord et al. ................. 250/338.5 |
| 6,560,545 | B2 | | 5/2003 | Stedman et al. |
| 6,671,630 | B2 | | 12/2003 | Stedman et al. |
| 6,701,256 | B2 | | 3/2004 | Stedman et al. |
| 6,723,989 | B1 | | 4/2004 | Didomenico et al. |
| 6,983,639 | B1 | | 1/2006 | DiDomenico et al. |
| 7,049,595 | B2 | * | 5/2006 | Kansakoski et al. ....... 250/338.5 |
| 7,071,002 | B1 | * | 7/2006 | Tefft et al. ..................... 436/137 |
| 7,131,319 | B2 | * | 11/2006 | Ganassi et al. ............. 73/118.01 |
| 7,164,132 | B2 | | 1/2007 | Didomenico et al. |
| 7,275,414 | B2 | | 10/2007 | Nelson, Jr. et al. |
| 7,305,870 | B2 | * | 12/2007 | Ganassi et al. ............. 73/116.01 |
| 2002/0052698 | A1 | | 5/2002 | Didomenico et al. |
| 2002/0194897 | A1 | | 12/2002 | Arnott et al. |
| 2003/0089854 | A1 | | 5/2003 | Shifflett et al. |
| 2003/0120434 | A1 | | 6/2003 | DiDomenico et al. |
| 2004/0155191 | A1 | | 8/2004 | Stedman et al. |
| 2006/0096394 | A1 | * | 5/2006 | Nelson et al. .............. 73/864.34 |
| 2007/0209544 | A1 | | 9/2007 | Caro et al. |

FOREIGN PATENT DOCUMENTS

| | | |
|---|---|---|
| WO | WO 92/12411 | 7/1992 |
| WO | WO 98/37405 | 8/1998 |
| WO | WO 02/082059 | 10/2002 |

OTHER PUBLICATIONS

Nelson, David D., et al., "High Precision Measurements of Atmospheric Nitrous Oxide and Methane Using Thermoelectrically Cooled Mid-Infrared Quantum Cascade Lasers and Detectors", *Spectrochimica Acta Part A*, 2004, pp. 1-11.

Houghton, J. T., et al.,"Climate Change 2001: The Scientific Basis", Contribution of Working Group I to the Third Assessment Report of the Intergovernmental Panel of Climate Change, First published 2001, pp. i-x.

The North American Carbon Program, NACP Committee of the U.S. Carbon Cycle Science Steering Group, 2002, pp. ii-v.

Nelson, D. D., et al., "Sub-Part-Per-Billion Detection of Nitric Oxide in Air Using a Thermoelectrically Cooled Mid-Infrared Quantum Cascade Laser Spectrometer", *Applied Physics B*, vol. 75, 2002, pp. 343-350.

Edwards, G. C., et al., "Eddy Correlation Measurements of Methane Fluxes Using a Tunable Diode Laser at the Kinosheo Lake Tower Site During the Northern Wetlands Study (NOWES)", *Journal of Geophysical Research*, vol. 99, No. D1, Jan. 20, 1994, pp. 1511-1517.

Wienhold, F. G., et al., "Measurements of $N_2O$ Fluxes from Fertilized Grassland Using a Fast Response Tunable Diode Laser Spectrometer", *Journal of Geophysical Research*, vol. 99, No. D8, Aug. 20, 1994, pp. 16,557-16,567.

Kosterev, Anatoliy A., et al., "Transportable Automated Ammonia Sensor Based on a Pulsed Thermoelectrically Cooled Quantum-Cascade Distributed Feedback Laser", *Applied Optics*, vol. 41, No. 3, Jan. 20, 2002, pp. 573-578.

Allan, David W., "Statistics of Atomic Frequency Standards", *Proceedings of the IEEE*, vol. 54, No. 2, Feb. 1966, pp. 221-230.

Hansen, James, et al., "Global Warming in the Twenty-First Century: An Alternative Scenario", *PNAS*, vol. 97, No. 18, Aug. 29, 2000, pp. 9875-9880.

Kormann, Robert, et al., "Eddy Flux Measurements of Methane Over the Fen 'Murnauer Moos', 11°11'E, 47°39'N, Using a Fast Tunable Diode Laser Spectrometer", *Atmospheric Environment*, vol. 35, 2001, pp. 2533-2544.

Werle, Peter, et al., "Fast Chemical Sensor for Eddy-Correlation Measurements of Methane Emissions from Rice Paddy Fields", *Applied Optics*, vol. 40, No. 6, Feb. 20, 2001, pp. 846-858.

McManus, J. Barry, et al., "Quantum Cascade Lasers for Open and Closed Path Measurement of Atmospheric Trace Gases", *SPIE*, 2002, Aerodyne Research, Inc., 12 pages.

Jimenez, J. L., et al., "Cross Road and Mobile Tunable Infrared Laser Measurements of Nitrous Oxide Emissions from Motor Vehicles", *Chemosphere—Global Change Science*, vol. 2, 2000, pp. 397-412.

Rothman, L. S., et al., "The HITRAN Molecular Spectroscopic Database: Edition of 2000 Including Updates Through 2001", *Journal of Quantitative Spectroscopy & Radiative Transfer*, 2003, pp. 1-39.

McManus, J. B., et al., "Astigmatic Mirror Multipass Absorption Cells for Long-Path-Length Spectroscopy", *Applied Optics*, 1994, 14 pages.

Sonnenfroh, David M., et al., "Application of Balanced Detection to Absorption Measurements of Trace Gases with Room-Temperature, Quasi-cw Quantum-Cascade Lasers", *Applied Optics*, vol. 40, No. 6, Feb. 20, 2001, pp. 812-820.

Werle, P., et al., "The Limits of Signal Averaging in Atmospheric Trace-Gas Monitoring by Tunable Diode-Laser Absorption Spectroscopy (TDLAS)", *Applied Physics B*, vol. 57, 1993, pp. 131-139.

Kosterev, Anatoliy A., et al., "Trace-Gas Detection in Ambient Air with a Thermoelectrically Cooled, Pulsed Quantum-Cascade Distributed Feedback Laser", *Applied Optics*, vol. 39, No. 36, Dec. 20, 2000, pp. 6866-6872.

Faist, J., et al., "Sensitive Absorption Spectroscopy with a Room-Temperature Distributed-Feedback Quantum-Cascade Laser", *Optics Letters*, vol. 23, No. 3, Feb. 1, 1998, pp. 219-221.

Kelly, Kerry, et al., "Black Carbon and Polycyclic Aromatic Hydrocarbon Emissions from Vehicles in the United States-Mexico Border Region: Pilot Study", Technical Paper, *Journal of the Air & Water Management Association*, vol. 56, Mar. 2006, pp. 285-293.

Kurniawan, A., et al., "Monitoring the Soot Emissions of Passing Cars", *Environmental Science & Technology*, vol. 40, No. 6, 2006, pp. 1911-1915.

\* cited by examiner

SYSTEM AND METHOD FOR QUANTIFYING THE PRESENCE OF COMPONENTS IN THE EXHAUST OF COMMERCIAL AND/OR HEAVY-DUTY VEHICLES

FIELD OF THE INVENTION

The invention relates generally to the quantification of the presence of one or more components in vehicle exhaust, and more particularly to a non-contact, extractive sampling system and method for quantifying the presence of one or more components in exhaust emissions of commercial and/or heavy-duty vehicles that emit exhaust at an elevated level, under actual operating conditions.

BACKGROUND OF THE INVENTION

Systems and methods for monitoring the exhaust gas composition and fine particle composition of exhaust emissions of various types of vehicles are known. For example, with regard to automobiles, it is common for emissions inspection stations (or automotive repair facilities) to utilize dynamometers for controlled engine loading tests for the purposes of exhaust emission measurement. One drawback associated with dynamometer testing, however, is that the measurements acquired often do not represent emissions under actual operating conditions when automobiles are in motion on a roadway or other driving surface.

To remedy these and other drawbacks associated with dynamometer testing, remote emissions sensing systems have been developed to remotely monitor the exhaust gas composition of automobiles traveling past "test sites" located along streets or highways. Examples of remote emissions sensing (or "cross-road") systems are described in, for example, U.S. Pat. Nos. 5,210,702, 5,319,199, 5,401,967, 5,591,975, 5,726,450, 5,797,682, 5,831,267, and 5,877,862, each of which is hereby incorporated herein by reference in its entirety.

However, existing systems configured to remotely test emissions tend to focus on passenger cars with exhaust systems that emit exhaust relatively close to the ground. By contrast, many commercial and/or heavy-duty vehicles, such as tractor-trailers, buses, commercial trucks, and/or other vehicles, have exhaust systems that emit exhaust at a point (or points) relatively high above the ground. For example, commercial diesel vehicles may include exhaust stacks that extend up vertically from the vehicles and emit exhaust up into the air.

As should be appreciated, exhaust leaving the exhaust pipe(s) of a moving commercial and/or heavy-duty vehicle (e.g., via exhaust "stacks" of a semi-tractor) is entrained in the vehicle's turbulent wake and continues to dissipate as the vehicle travels away. Despite the present turbulence, the dissipation of the exhaust will have a directionality associated with one or both of the location at which the exhaust is emitted and/or the direction in which it is propelled by momentum upon being emitted. For example, commercial and/or heavy-duty vehicles generally emit exhaust at an elevated position and/or propel emitted exhaust either upwards or to the side. As a result, remote emissions sensing systems designed to detect emissions for low-emitting vehicles (e.g., typical passenger automobiles) may not accurately quantify the presence of components in the exhaust of commercial and/or other heavy-duty vehicles.

Conventional remote sensing systems may further produce results that may not be indicative of the emissions of a commercial or heavy-duty vehicle because, depending on the placement of the remote sensing system and/or the operation of the commercial or heavy-duty vehicle, emissions from the vehicle may be measured while the vehicle is being operated in an atypical manner. For example, the emissions may be measured while the vehicle is changing gears. Measurements taken during a brief period of atypical operation may inaccurately indicate elevated levels of emission by the vehicle.

These and other problems can reduce the benefits of remote emissions sensing systems.

SUMMARY OF THE INVENTION

The invention addressing these and other drawbacks in the art relates generally to the quantification of the presence of one or more components in vehicle exhaust, and more particularly to a non-contact, extractive sampling system and method for quantifying the presence of one or more components in exhaust emissions of commercial and/or heavy-duty vehicles that emit exhaust at an elevated level (e.g., from a stack exhaust system), under actual operating conditions.

According to various implementations of the invention, to quantify the presence of one or more components in exhaust emissions of a commercial and/or heavy-duty vehicle that emits exhaust at an elevated level, a gathering structure and collector may be positioned directly over and/or adjacent to a path of the vehicle such that the gathering structure directs exhaust emitted by the vehicle at an elevated level above the roadway to the collector. The collector may receive at least a portion of the exhaust directed thereto by the gathering structure into one or more openings formed in the collector. A flow generator in fluid communication with the collector may generate a flow of air that draws exhaust directed to the collector by the gathering structure into the one or more openings of the collector. The flow of air generated by the flow generator may deliver the exhaust received into the one or more openings to a component detection system. Generally, the component detection system may quantify the presence in the exhaust of major gaseous exhaust species (e.g., concentrations of $CO_2$ or $H_2O$), along with the presence of one or more minor exhaust gases (e.g., carbon monoxide (CO), hycrocarbons (HC), oxides of nitrogen ($No_x$), etc.), and/or fine particulate matter present in the exhaust (e.g., quantified as smoke, opacity, particle mass, particle scatter, etc.) so that emission indices for the minor exhaust gases and/or fine particulate matter that represent the amount of pollutants in the exhaust above background levels may be deduced.

In certain implementations, the gathering structure may be disposed at or near the roadway, and may have at least one surface that causes exhaust emitted by the vehicle at an elevated level (e.g., from a stack exhaust system) to gather around the collector. The roadway may be an actual road lane, and/or may be a separate test lane. In some implementations, the gathering structure may include a roof that spans the path of the vehicle in the roadway, and the collector may be disposed such that the collector openings are located at or near an underside surface of the roof. In such implementations, exhaust ejected by the vehicle may be gathered and pooled around the collector openings by the underside surface of the roof, which may facilitate the reception of the exhaust into the collector openings. In some instances, the gathering structure may be impermeable to one or both of water and/or exhaust gases. In these instances, the gathering structure may further provide shelter for the collector openings and/or emitted exhaust from precipitation. Since the introduction of precipitation into the collector openings may interfere with the operation of the collector, the component detection system, and/or the flow generator generating the flow of air from the collector openings to the component detection system, the provision of shelter by the gathering structure may further enhance the collection and analysis of exhaust emitted by the vehicle at an elevated level.

According to various implementations, the gathering structure may include a tent-like structure. The roof of the gathering structure may be formed to guide exhaust that is emitted in a generally vertical direction toward the collector. For example, the roof of the gathering structure may be an "A-frame" roof, with the collector running along the underside of the roof at the interface between the two slopes of the "A-frame." The collector may be formed from a perforated pipe that runs along the underside of the roof at a position to which exhaust emitted in a substantially vertical direction is guided by the gathering structure.

In some implementations, the collector having one or more collector openings may be disposed along the path of the vehicle such that exhaust emitted by the vehicle at an elevated level (e.g., from a stack exhaust system) may be received into the one or more collector openings. The collector may include a conduit that communicates the received exhaust from the one or more collector openings to the component detection system that quantifies the presence of one or more components in the received exhaust.

In some implementations, the collector includes a plurality of collector openings that are arranged above the surface of a roadway along which the vehicle is traveling so as to receive the emissions of the vehicle, which are emitted at an elevated level (e.g., from high-stacks). For example, the collector may include a perforated pipe that forms the openings. In certain implementations, the collector may be disposed such that the collector openings are arranged along a path from between a first location and a second location that corresponds to the path of the vehicle between the first location and the second location. For example, the collector openings may be disposed in an array above the path of the vehicle between the first location and the second location to receive exhaust emitted upwards by the vehicle. This may facilitate the collection of exhaust by the collector openings, as exhaust emitted from the vehicle will be directed by momentum, turbulence, and/or other phenomena to the collector openings as the vehicle travels along the roadway.

According to some implementations, the flow generator may be configured to generate a flow of air that enables a continuous or periodic sampling of the air received into the collector openings at a predetermined flow rate. As the vehicle passes by the collector openings and exhaust from the vehicle is drawn into the collector openings toward the component detection system, the pressure in the conduit formed by the collector may decrease from atmospheric pressure at or near the collector openings, to a predetermined pressure level at a measurement space or cell associated with the component detection system where the presence of one or more components within the exhaust are quantified.

Characteristics of the collector and/or the collector openings (e.g., arrangement of the openings, length, diameter, cross-section, etc.), and/or operating parameters of the flow generator may be adjusted as necessary to achieve desired flow rates and pressure drops within the collector. Such adjustments to these and other components of the system may ensure that optimal conditions exist for quantifying the presence of one or more components in an exhaust sample delivered to the component detection system. Optimal conditions may vary depending on, for example, which molecular species of interest are being measured, as well as which type of component detection system is being implemented.

According to an implementation of the invention, the component detection system may comprise any system capable of quantifying the presence of one or more components in exhaust. For instance, the component detection system may include a trace gas detection system comprising one or more of a mass spectrometer, visible/ultraviolet absorption spectrometer, infrared absorption spectrometer, and/or other component detection instruments or systems. In some instances, the component detection system may include a fine particle measurement system comprising one or more of an aerosol mass spectrometer, condensation particle counter, light scattering detector, laser incandescent particle detector, and/or other fine particle instruments or systems.

The system and method of the invention as disclosed herein may be utilized to quantify the presence of one or more components in a plurality of samples of exhaust taken according to a predetermined sampling rate. In some instances, the quantification of the one or more components in the exhaust for the plurality of samples may be aggregated in order to provide an aggregated quantification of the one or more components in the exhaust emitted by the vehicle. The aggregated quantification may provide an enhanced accuracy and/or precision in determining the quantity and/or nature of the emissions of the vehicle. For example, even if the vehicle is being operated in some atypical fashion (e.g., changing gears) along the pathway, the aggregation of the quantification may suppress inaccuracies caused by this momentary atypical operation. In some instances, the aggregated quantification may be determined by averaging the quantifications of the presence of the one or more components in the plurality of exhaust samples.

According to one or more implementations, for a given test period (e.g., a pass of the vehicle past the collector openings and/or the gathering structure), a computer (or processor) may correlate a record (or data file) of quantification of the one or more components in the exhaust of the vehicle with a record of an identity, or other information, associated with the vehicle (e.g., registration information, etc.).

Both the record and vehicle identification/information may be stored in a memory associated with, or accessible by, the computer. Data regarding the identification of those vehicles passing by the collector openings and/or the gathering structure may be acquired by an imaging unit or other known identification device or system in operative communication with the computer (e.g., via a wireless or hard-wired connection). Other vehicle identification systems may be implemented.

Various other objects, features, and advantages of the invention will be apparent through the detailed description of the invention and the drawings attached hereto. It is also to be understood that both the foregoing general description and the following detailed description are exemplary and not restrictive of the scope of the invention.

DETAILED DESCRIPTION OF THE INVENTION

Figure 1:
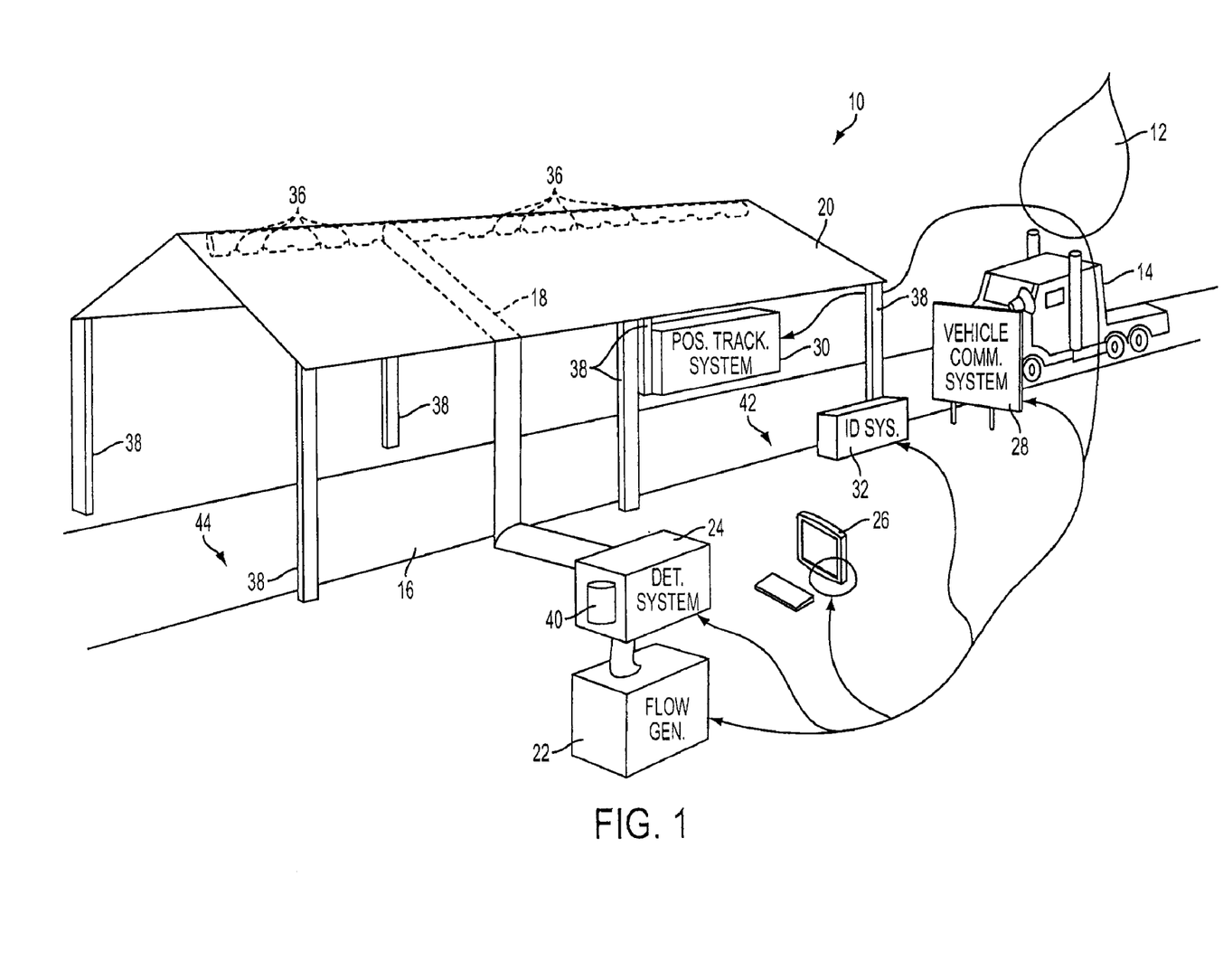
FIG. 1 illustrates a system for analyzing an exhaust plume of a vehicle traveling on a roadway, according to one or more implementations of the invention.

FIG. 1 illustrates a system 10 for analyzing an exhaust plume 12 of a vehicle 14 traveling on a roadway 16 under actual operating conditions, in accordance with one or more implementations of the invention. It should be appreciated that exhaust leaving the exhaust pipe(s) of moving vehicle 14 (e.g., via exhaust "stacks" of a semi-trailer or bus) is entrained in the vehicle's turbulent wake and continues to dissipate as vehicle 14 travels away. Despite the present turbulence, the dissipation of the exhaust will have a directionality associated with one or both of the location at which the exhaust is emitted and/or the direction in which it is propelled by momentum upon being emitted. For example, commercial and/or heavy-duty vehicles generally emit exhaust at an elevated position and/or propel emitted exhaust either upwards or to the side. As a result, remote emissions sensing systems designed to detect emissions for low-emitting vehicles (e.g., typical passenger automobiles) may not accurately quantify the presence of components in the exhaust of commercial and/or other heavy-duty vehicles.

Roadway 16 may comprise any driving surface suitable for safe passage of vehicle 14, and may further comprise a single vehicle travel lane, or multiple vehicle travel lanes. Roadway 16 may comprise a road along which vehicle 14 is traveling to its destination, or roadway 16 may comprise a separate test lane (or lanes) to which vehicle 14 has detoured from its route in order to have its emissions tested separate from other traffic. System 10 may be particularly suited to analyze exhaust where vehicle 14 is a semi-trailer truck, dump truck, tractor, bus, etc, that emits gas at an elevated level (in comparison with low emitting passenger vehicles), such as through a stack exhaust emission system.

In some implementations, system 10 may include one or more of a collector 18, a gathering structure 20, a flow generator 22, a component detection system 24, a computer 26, a vehicle communication system 28, a position tracking system 30, a vehicle identification system 32, and/or other components. As will be discussed further below, exhaust from exhaust plume 16 may be gathered by gathering structure 20 around collector 18, and pulled or extracted through collector 18, via suction generated by flow generator 22, to component detection system 24 where the presence of one or more components within the exhaust may be quantified. Upon analysis of the air provided to component detection system 24 through collector 18, the analyzed air may be exhausted from system 10 via an exit pipe.

According to various implementations, gathering structure 20 may have one or more surfaces that cause exhaust emitted by vehicle 14 to gather around one or more collector openings 36 formed in collector 18. Collector 18 may be disposed at or near such surfaces of gathering structure 20. This may facilitate the reception of exhaust into collector openings 36, as the exhaust gathered by gathering structure 20 remains concentrated around collector openings 36 for a relatively prolonged period of time, during which the gathered exhaust may be drawn into collector 18 via collector openings 36. In some instances, collector 18 may include a conduit, or conduits, formed integrally with gathering structure 20. In such instances, collector openings 36 may be formed as openings in a surface of gathering structure 20 that communicate with the conduit, or conduits, formed integrally with gathering structure 20.

In some implementations the one or more surfaces of gathering structure 20 that cause exhaust emitted by vehicle 14 to gather around one or more of collector openings 36 may be impermeable (or substantially so) for one or both of exhaust emitted by vehicle 14 and/or water. In such implementations, gathering structure 20 may protect collector openings 36 from precipitation. This may facilitate analysis of exhaust received by collector openings, as the introduction of ambient water from precipitation into exhaust may complicate one or both of transport of the exhaust by collector 18 and/or analysis of the collected exhaust.

In some instances, gathering structure 20 may include a roof. The roof may be positioned over some or all of roadway 16. The roof may provide the one or more of the surfaces that gather exhaust emitted by vehicle 14 around collector openings 36. The roof may be an "A-frame" roof, with collector 18 running along at or near the interface between the two planes that form the "A-frame" roof (or the "peak" of the roof). The roof may be supported a plurality of trusses (not shown). The trusses may run substantially perpendicular to the general direction of gathering structure 20. The roof may be supported above roadway 16 by one or more supports 38. Supports 38 may include one or more vertical structures with spaces in between and/or one or more solid vertical planes (e.g., walls).

In some implementations of the invention, collector 18 receives air from one or more collector locations above the surface of roadway 16. Collector 18 may be held in place at or near gathering structure 20 by one or more of a variety of different techniques for securing collector 18 in place. These techniques may include, for example, fastening collector 18 to gathering structure 20 with an adhesive and/or one or fasteners (e.g., one or more U-bolts), and/or other techniques. Collector 18 may include one or more conduits with one or more collector openings 36 formed therein. For example, collector 18 may be formed from one or more perforated pipes. Air can be drawn into collector 18 from ambient atmosphere via collector openings 36. Each of the collector openings 36 may form one of the aforementioned collector locations.

The position of collector openings 36 with respect to roadway 16 may facilitate reception by collector openings 36 of exhaust from vehicle 14 where vehicle 14 is a commercial or heavy-duty vehicle. For example, collector 18 is illustrated in FIG. 1 and discussed herein as providing collector openings 36 over roadway 16 to receive exhaust emitted at an elevated location and/or with an upward velocity by vehicle 14 (e.g., from the "stacks" on a semi-tractor, etc.). This is not intended to be limiting. For example, in some implementations, collector 18 may provide collector openings along side roadway 16 above the surface of roadway 16 (e.g., to collect exhaust emitted by vehicles that project exhaust out to the side). In certain implementations, collector 18 may include a single conduit along which collector openings 36 are formed (as shown in FIG. 1). In certain implementations, collector 18 may include a plurality of separate conduits and/or conduit branches, with each of the conduits and/or conduit branches forming one or more of collector openings 36.

In some implementations of the invention, collector openings 36 may be disposed between a first location and a second location on the roadway. The path between the first location and the second location may correspond to the path of vehicle 14 as it travels along roadway 16 (e.g., the path defined for vehicle 14 by roadway 16). For example, as may be seen in FIG. 1, in some implementations, collector openings 36 may be disposed above the path of vehicle 14 along the roadway to receive exhaust emitted by vehicle 14.

In some implementations of the invention, one or both of collector 18 and/or gathering structure 20 may be portable between sites. For example, collector 18 may be removable from gathering structure 20 to enable collector 18 to be selectively implemented at a plurality of different sites that have gathering structures. As another example, gathering structure 20 may include a tent-like structure, or some other portable structure that enables gathering structure 20 to be transported with collector 18 between sites.

Flow generator 22 may be in communication with collector 18, and may be configured to generate a flow of air within collector 18 that draws ambient air present at the collector locations into collector openings 36, and through the conduit(s) formed by collector 18. As such, flow generator 22 may generate a negative pressure at an end of the conduit(s) of collector 18 opposite collector openings 36 to create suction that draws the ambient air into collector openings 36. Flow generator 22 may include a vacuum pump, an impeller, and/or other flow generators capable of generating a flow of air from collector openings 36 down into the conduit(s) of collector 18.

In some implementations, flow generator 22 may be configured to continuously draw air into collector 18 at a predetermined flow rate (e.g., 5.0 standard liters per minute) from collector openings 36. As vehicle 14 passes by collector 18, a plug (or plugs) of air including a sample of exhaust plume 16 may be drawn through collector openings 36 and into the conduit(s) formed by collector 18. The air received thusly may be delivered from collector 18 to component detection system 24 (with which the conduit(s) of collector 18 is in fluid communication) for analysis, as is discussed below. The plug(s) of air including the exhaust sample remains essentially intact with minimal spreading as it travels through collector 18. The length of the conduit(s) between collector openings 36 and component detection system 24 may differ in various configurations as the distance between roadway 16 and component detection system 24, the height of collector openings 36 from the surface of roadway 16, and/or other system parameters vary.

At collector openings 36, air may be substantially at atmospheric pressure. As was mentioned above, to induce a flow of air within collector 18 that draws air into collector openings 36, flow generator 22 may generate a reduced pressure within collector 18 that falls to a predetermined pressure level at or near a measurement cell 40 associated with component detection system 24, at which the presence of one or more components in the air received from collector openings 36 may be quantified. In some instances, for example, the pressure in measurement cell 40 may decrease to approximately 50 torr.

In various implementations, characteristics of collector 18 (e.g., arrangement of openings, length, diameter, cross-section, etc.), and/or operating parameters of flow generator 22 may be adjusted as necessary to achieve desired flow rates and pressure drops within collector 18. Such adjustments to these and other components of system 10 may ensure that optimal conditions exist for quantifying the presence of one or more components in exhaust plume 14. Optimal conditions may vary depending on which components are being analyzed (e.g., which gaseous components, what size particulate matter, etc.), as well as what type of component detection system 24 is being implemented to best quantify the presence of the components of interest.

According to an implementation of the invention, component detection system 24 may comprise any system capable of quantifying the presence of one or more components in a sample of exhaust introduced into a measurement space or cell 40 (via collector 18 and flow generator 22). As such, component detection system 24 may comprise a detector capable of determining concentrations of one or more gaseous constituents of exhaust, a detector capable of measuring the density of particulate matter present in exhaust (e.g., opacity, smoke, etc.), and/or other detectors. For example, component detection system 24 may comprise a mass spectrometer, visible/ultraviolet absorption spectrometer, infrared absorption spectrometer, or other known or subsequently developed trace gas detection instrument or system. Similarly, component detection system 24 may comprise an aerosol mass spectrometer, condensation particle counter, light scattering detector, laser incandescent particle detector or other known or subsequently developed fast response, fine particle instrument or system.

According to one aspect of the invention, computer 26 may be in operative communication with and/or control one or more components of component detection system 24, flow generator 26, vehicle communication system 28, position tracking system 30, vehicle identification system 32, and/or other components. For example, computer 26 may control a data acquisition (or sampling) session, as well as process and store data from component detection system 24. Computer 26 may comprise a personal computer, portable computer (e.g., laptop computer), processor, or other device. In some implementations, computer 26 may comprise one or more of one or more processors, a user interface, memory, one or more storage devices, and/or other components, which are electrically coupled via a bus. The memory may comprise random access memory (RAM), read only memory (ROM), or other memory. The memory may store computer-executable instructions to be executed by the one or more processors, as well as data which may be manipulated by the one or more processors. The one or more storage devices may comprise floppy disks, hard disks, optical disks, tapes, or other storage devices for storing computer-executable instructions and/or data. The user interface may comprise interfaces to various peripheral devices (e.g., keyboard, mouse, microphones, external storage devices, monitors, printers or other input and/or output devices as would be appreciated by those having skill in the art) as well as other components as described herein.

According to one aspect of the invention, computer 26 may be connected by wire or wirelessly to a network (e.g., Internet, Intranet, etc.) so that emissions data or other information may be made accessible via a web site or other application (or transmitted a predetermined interval) to vehicle owners or operators, regulatory bodies (e.g., Dept. of Motor Vehicles), or to other entities.

In some implementations, component detection system 24 takes a plurality of "samples" of exhaust emitted by vehicle 14 adjacent to gathering structure 20. This may comprise quantifying the presence of one or more components (e.g., gaseous constituents, particulate matter, etc.) in air collected by collector 18 periodically at a sampling rate over a time period during which exhaust emitted by vehicle 14 while operating adjacent to gathering structure 20 is being analyzed. For example, this time period may include a time period during which exhaust emitted by vehicle 14 while traveling from a first location 42 at or near one end of gathering structure 20 to a second location 44 at or near the opposite end of gathering structure 20 is being analyzed by component detection system 24. In some instances, component detection system 24 (or some subsequent processor, such as computer 26) aggregates the samples taken during the time period to determine an aggregate quantification of the presence of the one or more components in the exhaust of vehicle 14. Even if the vehicle is being operated in some atypical fashion (e.g., changing gears) during the time period, the aggregation of the quantification may suppress inaccuracies caused by this momentary atypical operation, and may be more representative of the emissions of vehicle 14 under normal driving conditions that a conventional remote sensing measurement. For example, values determined for each of the samples may be averaged or otherwise aggregated to determine the aggregate quantification of the presence of the one or more components in the exhaust of vehicle 14.

In some instances, readings of component detection system 24 may be implemented as a "trigger" that causes an aggregation of measurements of exhaust components present in the air within collector 18. For example, a rise in $CO_2$, and/or some other exhaust component, in the air within collector 18 (as determined by component detection system 24) above some predetermined threshold may trigger the an aggregation of samples taken by component detection system 24. The aggregation may continue until the $CO_2$ within the air in collector 18 falls below the predetermined threshold, for a predetermined time period after the initial trigger, for a predetermined time period after the level of $CO_2$ falls below the threshold, and/or for some other amount of time.

As should be apparent from the configuration of collector 18 and gathering structure 20 with respect to roadway 16, system 10 is configured to detect the presence of components in the exhaust of vehicle 14 during normal operation of vehicle 14. Generally, the amount and composition of exhaust emitted by a vehicle is somewhat a function of the conditions under which the vehicle is operating. For example, exhaust emitted by vehicle 14 while cruising at freeway speeds on a level grade would be expected to be different in quantity and/or composition from exhaust emitted by vehicle 14 while accelerating from a stopped position.

As such, vehicle communication system 28 may be provided to communicate with the driver of vehicle 14 the manner in which vehicle 14 should be operated while it is traveling along the path of roadway 16 that is adjacent to collector openings 36 (e.g., underneath collector openings 36 between first location 42 and second location 44). For example, vehicle communication system 28 may communicate instructions to the driver of vehicle 14 dictating the manner in which vehicle 14 should be operated. In one implementation, the instructions may include: (1) an instruction to bring vehicle 14 to a stop, or some predetermined low speed, at first location 42 at one end of gathering structure 20; and (2) an instruction to accelerate from the stop (or low speed) while traveling along the roadway adjacent to gathering structure 20 toward second location 44. The instruction to accelerate may include a predetermined upper speed that vehicle 14 should reach before exiting the section of roadway adjacent to gathering structure 20 (e.g., at second location 44), a rate of acceleration, and/or other instructions that specify how much vehicle 14 should accelerate. In one implementation, the instructions may include a speed at which vehicle 14 should be driven for the entire time that it is on roadway 16 between first location 42 and second location 44. Other implementations, in which vehicle communication system 28 communicates other operating conditions to the driver of vehicle 14 exist.

In order to communicate with the driver of vehicle 14, vehicle communication system 28 may include one or more displays, one or more speakers, and/or other interfaces that communicate information to the driver of vehicle 14. In some implementations, the one or more displays may include one or more dynamic, electronic displays (e.g., monitors, screens, projectors, lights, etc.) that can be controlled to provide information to the driver of vehicle 14. In some implementations, the one or more displays may include one or more static, fixed displays (e.g., signs, lettering/figures formed on roadway 16, lettering/figures formed on gathering structure 20, etc.), and/or other displays.

Although vehicle communication system 28 may be positioned proximate to gathering structure 20 and/or collector 18, in some implementations, vehicle communication system 28 may provide communication to the driver of vehicle 14 at some predetermined distance from gathering structure 20 and/or collector 18. For example, at some predetermined distance from gathering structure 20 and/or collector 18, vehicle communication system 28 may communicate to the driver of vehicle 14 that a test zone at which the emissions of vehicle 14 will be tested is upcoming, and that vehicle 14 should achieve and/or maintain some predetermined speed while adjacent to gathering structure and/or collector 18.

In some implementations of the invention, position tracking system 30 may track the position, speed, acceleration, jerk, etc. of vehicle 14 as it travels along roadway 16 between first location 42 and second location 44. Position tracking system 30 may include one or more of infrared motion sensors, pressure sensors, radar, lidar, sonar, and/or or other sensors capable of detecting the presence, speed, acceleration, etc. of vehicle 14.

The information determined by position tracking system 30 may be communicated to computer 26, and may be processed by computer 26 to determine the compliance of vehicle 14 with the instructions provided by vehicle communication system 28. This may enable computer 26 to "flag" instances where vehicle 14 has not been operated in accordance with the operating conditions dictated by vehicle communication system 28 (e.g., as invalid, as being of questionable accuracy and/or precision, etc.).

In some instances, the information determined by position tracking system 30 may be implemented to determine when exhaust emitted by vehicle 14 is being analyzed by component detection system 24 (as opposed to ambient air). For example, as was mentioned above, there is generally a delay between the reception of exhaust at collector openings 36 and introduction of the received exhaust into component detection system 24 (e.g., within measurement cell 40). The detection of the position of vehicle 14 along roadway 16, coupled with a known amount of time associated with this delay may enable a determination (e.g., by computer 26) as to when the exhaust emitted by vehicle 14 and received at collector openings has reached component detection system 24.

In some implementations, information related to the position of vehicle 14 by position tracking system 30 may be implemented to "trigger" operation of one or both of flow generator 22 and/or component detection system 24. For example, a determination by position tracking system 30 that vehicle 14 is at or approaching gathering structure 20 (e.g., at or approaching first location 42) may trigger flow generator 22 to begin to generate a flow of air from collector openings 36 to component detection system 24. In such instances, flow generator 22 may begin to generate a flow by opening a valve (e.g., to communicate the conduit(s) associated with collector 18 with a reduced pressure chamber), initiating a pump (e.g., to begin suction), and/or otherwise generating a flow from collector openings 36 to component detection system 24. Similarly, flow generator may cease the generation of a flow from collector openings 36 to component detection system upon a determination by position tracking system 30 that vehicle 14 is exiting, or has exited, gathering structure 20.

Data regarding the identification of those vehicle 14 passing adjacent to gathering structure 20 to have its exhaust tested may be acquired by vehicle identification system 32 or other known identification device or system (not illustrated) in operative communication with computer 26 (e.g., via a wireless or hard-wired connection). Vehicle identification system 32 may comprise, for example, a film camera, video camera, or digital camera. Other imaging devices may also be used. Preferably, the imaging unit associated with vehicle identification system 32 may record an image of the identification tag (e.g., license plate) of vehicle 14. Tag information may be processed by computer 26 to provide additional information about vehicle 24. For example, a Motor Vehicle Department databases may be accessed to retrieve owner information, driver information, license information, make, model type, model year, or other information.

According to one implementation of the invention, an identification tag on vehicle 14 may be read by vehicle identification system 32 to identify the vehicle, and computer 26 may associate particular sensed vehicle emission information with the identified vehicle. In some implementations, an identification tag (defined as a license plate above), may comprise a transponder located on or within vehicle 14 (e.g., hung from a rear view mirror, placed on the dashboard, etc.), or that is integral within the vehicle (e.g., part of a global positioning system ("GPS"), located within the engine of the vehicle, or placed or mounted elsewhere). The transponder may transmit information about vehicle 14, including make and model of vehicle 14, engine characteristics, fuel type, the owner of vehicle 14, or other information which may be pertinent. Information transmitted by the transponder may be received by vehicle identification system 32. According to an implementation of the invention, a transponder may be used in connection with other functions. By way of example, a transponder may also be used in connection with a toll pass, whereby a driver can electronically pay tolls via the transponder without stopping the vehicle.

An identification tag may also comprise a tag or decal that requires a reader associated with vehicle identification system 32. By way of example, an identification tag may comprise a decal with identifying marks (e.g., bar codes, infrared markings, etc.) containing information about vehicle 14. The decal may be located outside vehicle 14, such as on a front or rear bumper, on the under-side of vehicle 14, or any other location on vehicle 14 where the decal may be suitably read. A reader may observe the decal and thereby obtain information about vehicle 14.

Computer 26 may receive information about vehicle 14 from a reader and/or receiver associated with vehicle identification system. Vehicle information and information obtained by sensing vehicle emissions may be stored. Computer 26 may correlate vehicle information received from an identification tag with the results from vehicle emissions sensing. Computer 26 may update a vehicle record to include results obtained by processing vehicle emission data, such as information regarding whether a vehicle has passed or failed predetermined emissions criteria. Other vehicle identification systems may be implemented.

Figure 2:
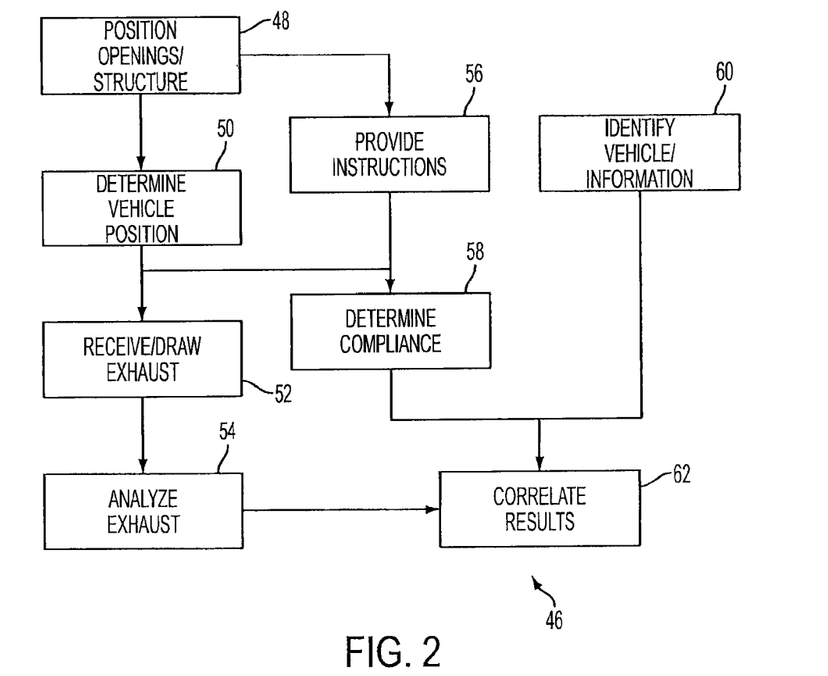
FIG. 2 illustrates a method of quantifying the presence of one or more components in an exhaust plume of a vehicle traveling on a roadway, in accordance with one or more implementations of the invention.

FIG. 2 illustrates a method 46 of quantifying the presence of one or more components in an exhaust plume of a vehicle traveling on a roadway, in accordance with one or more implementations of the invention. Although some of the operations of method 46 are discussed below with respect to the components of system 10 described above and illustrated in FIG. 1, it should be appreciated that this is for illustrative purposes only, and that method 46 may be implemented with alternative components and/or systems without departing from the scope of this disclosure. Further, the particular arrangement of the operations illustrated in FIG. 2 and described hereafter is not intended to be limiting. In some implementations, various ones of the operations could be performed in an order other than the one set forth, various ones of the operations may be combined with others and/or be omitted altogether, and/or various additional operations may be added without departing from the scope of the disclosure, as should be appreciated.

At an operation 48, one or more openings of a collector and/or a gathering structure may be positioned above the surface of the roadway such that one or more surfaces of the gathering structure may cause exhaust emitted by the vehicle as it travels on the roadway to gather around the one or more openings of the collector. In some implementations, the collector and/or the gathering structure may be similar to or the same as collector 18 and/or gathering structure 20, shown in FIG. 1 and described above.

At an operation 50, information related to the position of the vehicle is determined. The information related to the position of the vehicle may include one or more of the position, speed, acceleration, and/or jerk of the vehicle. The information determined at operation 50 may include one or both of information related to the position of the vehicle with respect to the gathering structure and/or collector openings positioned at operation 48, and/or the operating conditions under which the vehicle is operating while it is adjacent to the gathering structure and/or collector openings. In some implementations, operation 50 may be performed by a position tracking system that is the same as or similar to position tracking system 30, shown in FIG. 1 and described above.

At an operation 52, exhaust emitted by the vehicle may be received into the plurality of collector openings. Receiving the exhaust into the plurality of collector openings may include generating a flow of air from the collector openings into the collector that draws the exhaust into the collector by way of the collector openings. The flow of air may be created via suction within the collector. In some instances, the generation of the flow of air may be triggered by a determination of the position of the vehicle at operation 50 (e.g., that the vehicle is at or approaching the gathering structure and/or collector openings). In some implementations, the flow of air may be generated by a flow generator that is the same as or similar to flow generator 22, shown in FIG. 1 and described above.

At an operation 54, exhaust received into the collector openings at operation 52 may be analyzed to quantify the presence of one or more components in the received exhaust. The exhaust may be delivered from the collector openings to a component detection system by the flow of air generated at operation 52, and the component detection system may perform the analysis of the received exhaust at operation 54. In some instances, the analysis of the presence of components in air received at operation 52 into the collector openings may be triggered by a determination of the position of the vehicle at operation 50 (e.g., that the vehicle is at or approaching the gathering structure and/or collector openings). In some implementations, the component detection system may include a component detection system that is the same as or similar to component detection system 24, shown in FIG. 1 and described above.

At an operation 56, instructions may be provided to the vehicle that dictate the manner in which the vehicle should be operated when it is adjacent to the gathering structure and/or collector openings positioned at operation 48. In some instances, the instructions may be dynamic (e.g., delivered via an electronic display and/or speaker. In some instances, the instructions may be static (e.g., delivered via signage). In some implementations, operation 56 may be performed by a vehicle communication system that is the same as or similar to vehicle communication system 28, shown in FIG. 1 and described above.

At an operation 58, compliance of the vehicle with the instructions provided to the vehicle at operation 56. The compliance of the vehicle with the provided instructions may be based on information related to the position, speed, acceleration, and/or jerk of the vehicle determined at operation 50. In some implementations, operation 58 may be performed by a computer that is similar to or the same as computer 26, shown in FIG. 1 and described above.

At an operation 60, the vehicle and/or vehicle information related to the vehicle (e.g., owner information, driver information, license information, make, model type, model year, etc.) may be identified. In some implementations, operation 60 may be performed by a vehicle identification system that is the same as or similar to vehicle identification system 32, shown in FIG. 1 and described above.

At an operation 62, results of the analysis performed at operation 54 may be correlated with one or both of compliance information determined at operation 58 and/or vehicle information identified at operation 60. This may create a record that relates results of the analysis with the appropriate vehicle (and/or class of vehicle), and/or specifies at least some of the parameters under which testing was conducted (e.g., whether the vehicle complied with the instructions provided at operation 58 during the testing).

Figure 3:
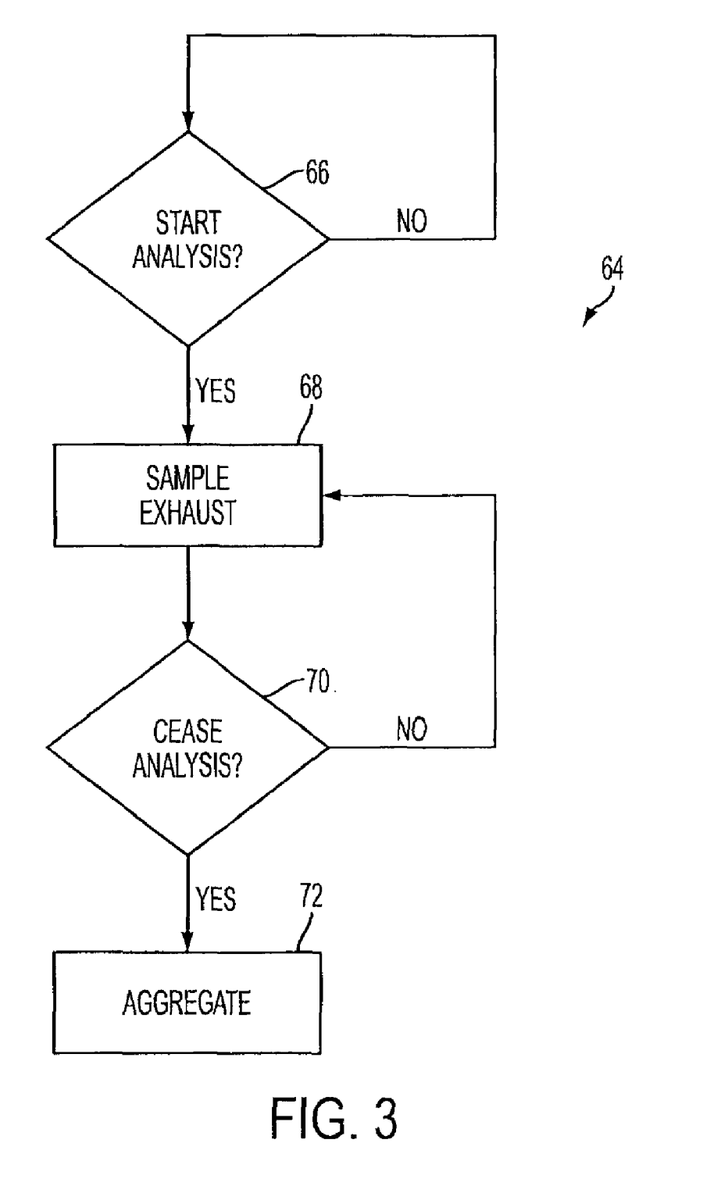
FIG. 3 illustrates a method of analyzing exhaust to quantify the presence of one or more components in the exhaust, according to one or more implementations of the invention.

FIG. 3 illustrates a method 64 of analyzing exhaust to quantify the presence of one or more components in the exhaust, according to one or more implementations of the invention. In the description of method 64 and one or more of its operations below, specific reference is made to various components shown in FIG. 1 and described above and/or various operations shown in FIG. 2 and described above. However, this should not be viewed as limiting. Instead, method 64 should be appreciated as being usable with a variety of different systems and methods. Further, the particular arrangement of the operations of method 64 illustrated in FIG. 3 and described hereafter is not intended to be limiting. In some implementations, various ones of the operations could be performed in an order other than the one set forth (or concomitantly with other ones of the operations), various ones of the operations may be combined with others and/or be omitted altogether, and/or various additional operations may be added without departing from the scope of the disclosure, as should be appreciated.

At an operation 66, a determination may be made as to whether analysis of the exhaust should begin (or has begun). Operation 66 may include determining whether exhaust received into collector openings adjacent to a roadway along which a vehicle is traveling has reached a component detection system performing the analysis. For example, operation 66 may include determining whether exhaust received at operation 52 of method 46, shown in FIG. 1 and described above, has reached the component detection system. The determination made at operation 66 may be based on a position of the vehicle (e.g., at operation 50 of method 46) and/or a known delay time between the reception of the exhaust into the collector openings and the arrival of the received exhaust at the component detection system. In some implementations, operation 66 may be performed by a computer that is the same as or similar to computer 26, shown in FIG. 1 and described above.

If the determination is made at operation 66 that analysis of the exhaust should not (or has not) begun, method 64 performs operation 66 yet again. If the determination is made at operation 66 that analysis of the exhaust should begin, then method 64 proceeds to an operation 68, at which the exhaust is sampled to quantify the presence of one or more components. In some instances, this may include taking a single measurement of the one or more components and proceeding to an operation 70. In some instances, this may include taking a series of samples at a predetermined sampling interval and then proceeding to operation 70. In some implementations, operation 68 may be performed by a component detection system that is the same as or similar to component detection system 24, shown in FIG. 1 and described above.

At operation 70, a determination may be made as to whether analysis of the exhaust should cease (or has ceased). Operation 70 may include determining whether exhaust received into collector openings adjacent to a roadway along which a vehicle is traveling is no longer reaching component detection system performing the analysis (e.g., because the vehicle has passed the collector openings). For example, operation 70 may include determining whether all of the exhaust received at operation 52 of method 46, shown in FIG. 1 and described above, has already been sampled and exhausted by the component detection system. The determination made at operation 70 may be based on a position of the vehicle (e.g., at operation 50 of method 46) and/or a known delay time between the reception of the exhaust into the collector openings and the arrival of the received exhaust at the component detection system. In some implementations, operation 70 may be performed by a computer that is the same as or similar to computer 26, shown in FIG. 1 and described above.

If the determination is made at operation 70 that analysis of the exhaust should not cease (or has not ceased), method 64 may return to operation 68. If the determination is made at operation 70 that analysis of the exhaust should cease (or has ceased), then method 64 may proceed to an operation 72.

At operation 72, the samples quantifying the presence of the one or more components in the exhaust, taken at operation 68, are aggregated by one or more of several possible mathematical techniques to provide an aggregate quantification of the presence of the one or more components in the exhaust of the vehicle. In some instances, operation 72 may include averaging the samples. In some implementations, operation 72 may be performed by a computer that is the same as or similar to computer 26, shown in FIG. 1 and described above.

Although the invention has been described in detail for the purpose of illustration based on what is currently considered to be the most practical and preferred implementations, it is to be understood that such detail is solely for that purpose and that the invention is not limited to the disclosed implementations, but, on the contrary, is intended to cover modifications and equivalent arrangements that are within the spirit and scope of the appended claims. For example, it is to be understood that the present invention contemplates that, to the extent possible, one or more features of any implementation can be combined with one or more features of any other implementation Other implementations, uses and advantages of the invention will be apparent to those skilled in the art from consideration of the specification and practice of the invention disclosed herein. The specification should be considered exemplary only, and the scope of the invention is accordingly intended to be limited only by the following claims.

What is claimed is:

1. A system, positioned at a site along a roadway, for determining the concentration of one or more constituents present in a sample of exhaust emissions emitted by a vehicle traveling on the roadway, the system comprising:
    a component detection system configured to determine the concentration of one or more constituents present in vehicle exhaust emissions;

a gathering structure comprising a roof that is supported above the surface of the roadway by one or more supports such that the vehicle can pass under the roof while traveling along the roadway;

a collector, operatively coupled to the component detection system, that is disposed on an underside of the roof of the gathering structure and oriented in a direction parallel to a direction of travel of the roadway, the collector having one or more openings for receiving the exhaust emissions of the vehicle to be analyzed by the component detection system, wherein the roof of the gathering structure pools the exhaust emissions from the vehicle to be analyzed by the component detection system near the one or more openings of the collector prior to measurement by the component detection system; and wherein the component detection system is configured to receive a sample of the exhaust emissions of the vehicle via the collector, and to determine the concentration of one or more constituents present in the sample of exhaust emissions.

2. The system of claim 1, wherein the roadway comprises a test lane.

3. The system of claim 1, wherein the roadway comprises a single vehicle travel lane, and wherein the roof of the gathering structure covers the single vehicle travel lane.

4. The system of claim 1, wherein the roadway comprises multiple vehicle travel lanes, and wherein the roof of the gathering structure covers one of the multiple vehicle travel lanes.

5. The system of claim 1, wherein the roadway comprises multiple vehicle travel lanes, and wherein the roof of the gathering structure covers the roadway.

6. The system of claim 1, wherein the collector comprises a perforated pipe.

7. The system of claim 1, wherein the collector is fastened to the underside of the roof.

8. The system of claim 1, wherein the one or more openings of the collector face the surface of the roadway.

9. The system of claim 1, wherein the collector is integrally formed with the roof of the gathering structure such that the one or more openings of the collector comprise one or more openings in the underside of the roof of the gathering structure.

10. The system of claim 1, wherein the one or more supports of the gathering structure comprise at least one wall on a first side of the roadway and at least one wall on an a second side of the roadway that is opposite the first side of the roadway.

11. The system of claim 1, wherein the roof comprises an A-frame roof defined by two planes oriented at an angle to one another, and wherein the collector is disposed on the underside of the roof at or near the intersection of the two planes.

12. The system of claim 1, wherein the roof is impermeable to the exhaust emissions.

13. The system of claim 1, wherein the roof is water-proof.

14. The system of claim 1, further comprising:
a flow generator, in communication with the collector, that is configured to generate a flow of air that draws the sample of the exhaust emissions to the component detection system.

15. The system of claim 1, wherein the component detection system is located remotely from the roadway.

16. The system of claim 1, wherein the component detection system comprises a trace gas detection system.

17. The system of claim 1, wherein the component detection system comprises a fine particle measurement system.

18. The system of claim 1, further comprising:
a vehicle communication system including at least one display, wherein the at least one display communicates information to a driver of the vehicle as the vehicle is approaching the gathering structure.

19. The system of claim 1, further comprising:
a vehicle identification system configured to capture an image of a license plate of the vehicle.

20. The system of claim 1, further comprising:
a position tracking system for tracking one or more of the position, speed, or acceleration of the vehicle.

21. The system of claim 1, further comprising:
a computer, operatively connected to the component detection system and to a network, wherein the computer is configured to:
receive, from the component detection system, information concerning the concentration of one or more constituents present in the sample of exhaust emissions; and
transmit the received information to a network location via the network.

* * * * *